Figure 1:
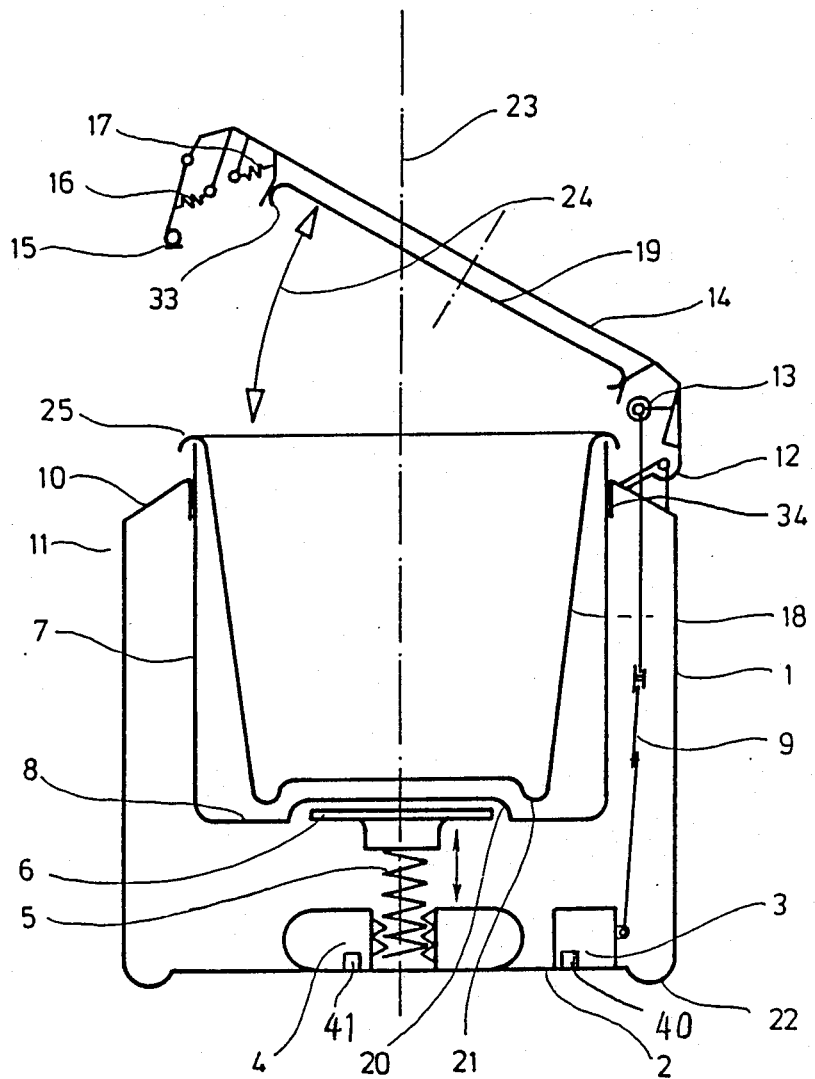

United States Patent [19]

Löbbert

[11] Patent Number: 4,883,189

[45] Date of Patent: Nov. 28, 1989

[54] DEVICE FOR HYGIENIC WASTE COLLECTION IN HOSPITALS, LABORATORIES AND SIMILAR ESTABLISHMENTS

[76] Inventor: Johannes Löbbert, Herteler 54, D-4420 Coesfeld, Fed. Rep. of Germany

[21] Appl. No.: 223,073

[22] PCT Filed: Nov. 13, 1987

[86] PCT No.: PCT/EP87/00702
§ 371 Date: Jul. 12, 1988
§ 102(e) Date: Jul. 12, 1988

[87] PCT Pub. No.: WO88/03416
PCT Pub. Date: May 19, 1988

[30] Foreign Application Priority Data

Nov. 14, 1986 [DE] Fed. Rep. of Germany ... 8630535[U]

[51] Int. Cl.⁴ .............................................. B65F 1/08
[52] U.S. Cl. .................................. 220/1 T; 220/211; 220/260
[58] Field of Search .............. 220/1 T, 211, 256, 260, 220/262, 263

[56] References Cited

U.S. PATENT DOCUMENTS 4,489,810 12/1984 Curtis .............................. 220/211 X
4,552,720 11/1985 Baker, Sr. et al. .

FOREIGN PATENT DOCUMENTS 3317300 11/1984 Fed. Rep. of Germany .

Primary Examiner—Gerald A. Michalsky
Attorney, Agent, or Firm—Cushman, Darby & Cushman

[57] ABSTRACT

Disposal equipment for infectious or otherwise contaminated waste, to be used for instance in hospitals, doctors' offices, laboratories and similar institutions; the waste is disposed of in a container (18) placed on a support (1); when the container (18) is full, it is closed tight by means of the lid (19) provided. The release-ready lid (19) is held on the support (1) by means of the rotating lid holder (14) which is actuated by the motorized drive. The opening and closing of the container is provided by the lid holder (14), and during the filling phase the lid (19) is closed down loosely on the container (18). When the container is full, another drive (4, 5) linked to the equipment (1) closes the lid holder (14) with the lid down tight onto the container, and the lid (19) connected to the container (18) is then released.

10 Claims, 2 Drawing Sheets

DEVICE FOR HYGIENIC WASTE COLLECTION IN HOSPITALS, LABORATORIES AND SIMILAR ESTABLISHMENTS

The invention consists of a pick-up equipment for infectious or otherwise contaminated waste, to be used for instance in hospitals, doctors' offices, laboratories and similar institutions; the waste is disposed of in a container held by a support, and when the container is full it is closed tight by means of the lid provided.

Medical waste, such as those found in hospitals, doctors' offices, laboratories or similar institutions, can be very infectious. Such waste must be collected, stored and disposed of, without risking the release of further contamination, whether during collection, storage or disposal. In the said institutions, the waste has usually been disposed of in open plastic bags, or manually thrown into plastic containers. When full, these are closed tight by hand or with a lid and finally taken away for incineration.

It has been shown that this method of disposal is hazardous, first because of the manual interventions, and second due to the opening and closing by hand of the plastic containers, which causes turbulence in the air mass above the container during disposal and closing. This may help disease carriers enter the environment. The closing and opening result in the airborne transportation of poison or pathogenic disease carriers from within the container.

Therefore, the hazards of this technique should be removed and replaced by equipment for the hygienic disposal of waste, which would avoid as much as possible contact with the waste container and completely prevent any spreading of disease carriers, while making use of well-known containers. The container must be closed tight without any risk of contamination. Any infection hazard due to the airborne transportation of micro-organisms or toxic dust must be avoided as much as possible.

These requirements are met by the equipment described above, whose specific feature is the release-ready lid held on the support by means of the rotating lid holder which is actuated by the motorized drive and which provides the opening and closing of the container, while the lid is shut down loosely on the container during the filling phase; another drive linked to the device closes the lid holder with the lid down tight onto the container, and releases the lid once it has been connected to the container.

The equipment carries out two different functions which are both essential to the operation. First, the lid holder is raised by motor with the lid almost in slow-motion, which experience shows excludes the possibility of turbulence. The lid holder is always activated when new waste is thrown into the container. The second function consists of keeping the lid ready for closing in the lid holder: during the filling phase it is always closed loosely on the container, and when the container is full it is pressed tight on the container by means of the lid holder and the support. Therefore, in the corresponding lid-container assembly the container clamps onto and covers the lid, therefore ensuring a secure closing. This operation is done while the equipment is closed; it is fully automatic.

The container can have a beaded edge. This is important if the support includes an open pick-up receptacle fixed under the beaded edge of the container, which carries the container even when significant forces are applied.

The container can be raised and lowered alone or with the pick-up receptacle. The bottom of the receptacle can be fitted with a hydraulic piston, a screw spindle or a brace stool. These applications are well-known from specialists of research techniques and are possible constructive solutions.

To maintain the container and to have a smooth operation, the bottom of the receptacle is moulded on the shape of the plate, which is raised and lowered by a drive.

The lid holder is fitted with spring clamps or alternatively rubber clamps. The lid can be simply placed in these clamps, and it is then automatically removed. The clamping force is set so that the lid, which is tightly fitted on the container, can be released from the clamps.

The lid holder is tilted by means of a motorized drive, and an intermediate drive ensures that the tilting is very slow. A sliding gear can be used.

All devices can be independently supplied from a power source. The raising and lowering of the lid can be activated by a pedal-driven hydraulic pump. The support can also be fitted with a moving, removable clamp assembly, which fits into the corresponding parts of the lid holder and which pulls the lid holder against the support; this can be activated by the pedal. It is also possible to build the equipment on the basis of that design but with parts which are independent from an external power source. But the best technical solution should result in a device which prevents human intervention through the use of electric power, and which avoids manual contact, specifically the operation of heavy and cumbersome pedals, as well as uncontrolled movements of the lid and therefore contamination.

Applications of the invention are shown in the drawing. The figures show the following:

FIG. 1 Schematic cross-section of equipment with the first application

Figure 2:
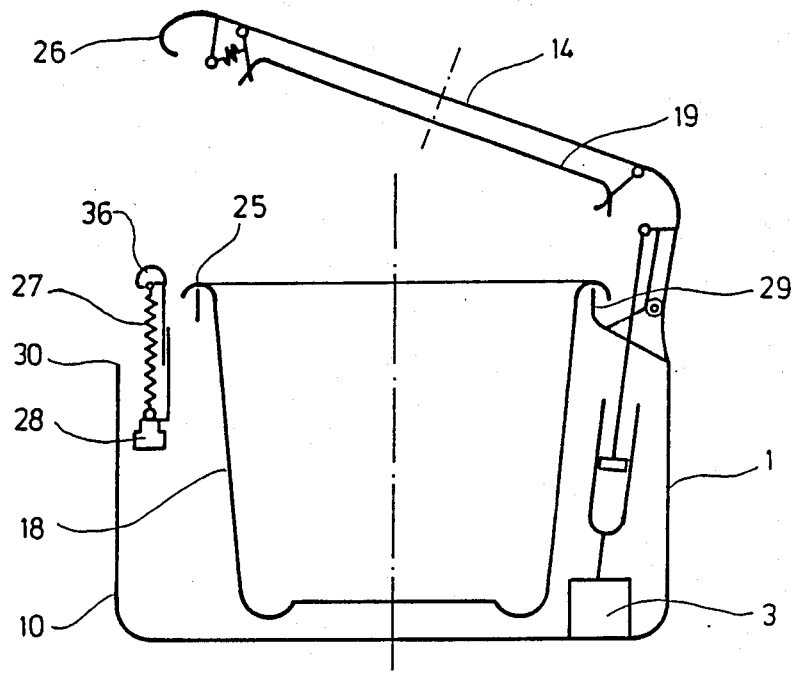

FIG. 2 Second application

Figure 3:
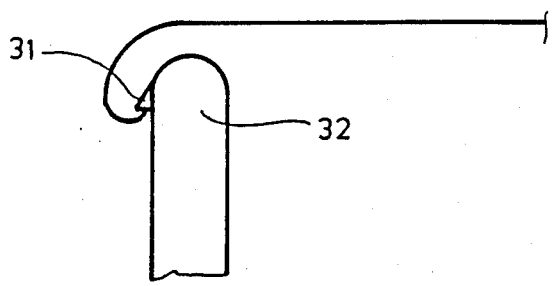

FIG. 3 Detail of the lid assembly

The equipment for the hygienic disposal of infectious or otherwise contaminated waste, to be used for instance in hospitals, doctors' offices, laboratories and similar institutions, has been designed so that its height facilitates access to the container inside the equipment. The equipment can be set up accordingly, or installed underground. It is fitted with a removable container (18), which may be shaped like a truncated cone. The container is made of a plastic material such as polyethylene. It is held on a support (1), which includes an enclosed chassis (10) with a bottom (2). The outer part of the support may be shaped like a cylinder or a polygonal prism, or similar. Inside the chassis (10) there is a pick-up receptacle (7), which can be an enclosed plastic or sheet-metal cylinder; here, as well, hygienic requirements are paramount. The top of the receptacle (7) fits under the beaded edge (25) of the container (18) which becomes its top. Therefore the container hangs inside the receptacle (7).

The receptacle (7) can also be tightly connected with the rest of the support. In this case, a construction should be chosen in which the receptacle (7) carried by the container (18) can be raised and lowered. The receptacle (7) is carried inside a collar (34) formed by the outer liner of chassis (10). Under the receptacle (7) there is an arch (20) which reaches the inside the receptacle (7), allowing it to fit tightly on a plate (6). The plate (6)

can be raised and lowered on an axle (23) by means of a drive (schematically illustrated), which consists of a spindle (5) and a drive motor (4). The motor (4) can be activated by a switch (41) fitted on the chassis (not illustrated), and the plate cannot be raised or lowered beyond a pre-set limit. As already mentioned, instead of the spindle drive (4, 5), another elevating device can be installed, such as hydraulic or pneumatic piston-cylinder assemblies, by means of an adjustable, spindle-driven stool, or equivalent. The bottom (8) of the receptacle (7) can be raised or lowered with the container.

Another important feature of the invention is the lid holder (14), which can be tilted and is connected to the support (1). This is done through the tilting joint (12), which moves the lid holder (14) in the direction indicated by the arrow (24). The tilting is not activated by pedal or by hand, but by the drive motor (3), which may actuate the swivel (13) through an eccentric drive and rod (9) assembly called the sliding drive, and the opening and closing are achieved by means of a fixed-cycle switch (40). Generally, a foot switch is installed. Proximity switches, acoustically activated switches or equivalent can also be used. Such switch elements are known by specialists. The opening and closing of the lid is slow and almost occurs in slow-motion, therefore avoiding any dangerous turbulence in the air between the lid holder and the container opening.

Under lid holder (14), a removable container lid (19) is kept in a clamping device, which is schematically represented by a clamp (17). As long as the container (18) is not full, the lid holder (14) opens and closes with the lid (19), closing the lid (19) down loosely on the container. When lid holder (14) opens, the lid is always lifted. When the container (18) is full and ready to be removed, the lid holder (14) is kept in its horizontal position. The drive motor (4) starts up and lifts the holding device with the container against the stopped lid holder (14). The lid is pressed against the container. The lid edge (33) covers the beaded edge (25) of the container, making an audible "click". The lid is now closed tight and can only be separated from the container (18) by applying considerable strength. If the lid holder (14) is tilted upwards, the lid is released from the clamps. Finally, the container is removed, manually or by means of a vacuum transportation device. A new lid can be fitted in the lid holder (14).

In specified applications, containers with lids which can be securely closed should be used. These cylindrical disposable containers made of plastic or metal are used for the final destruction or storage of their contents. Unauthorized tampering with or removal of the contents must be avoided. Snap closures which are difficult to open should be used. The beaded edge (25) of the container (18) and the corresponding lid edge (33) are used, and closing is done with a relatively long axial movement while strength is applied along the axis (23).

The construction of the beaded edge (25) of container (18) can also include fitting the upper edge of receptacle (7) with specific features, such as slots and pegs. This ensures that only certain authorized containers can be used, and only in certain positions. Therefore, the support (1) and its supporting and/or supported parts are only suitable for one type of container.

The lid holder (14) has relatively low-cut edges, with beaded-edge bearing surfaces (15), which can be pressed by means of a spring (16). The advantage is that the lid is pressed tightly against the outside (11) of the chassis (1).

FIG. 2 shows a simplified application. It also includes a support (1), inside of which a container (18) is hanging. However, the container cannot be raised and lowered. The lid holder (14), with the lid (19) fitted in it, is driven by drive motor (3). This application applies a similar technique to the application shown in FIG. 1. The beaded edge (25) of the container (18) is carried by a lower support (29).

A bevel (30) of the chassis (10) is fitted with a clamp (27) which has a hook (36) pulling downwards by means of a spring. The pulling can be done by a knob (28). The knob can be replaced by a pedal or equivalent. When the lid holder (14) is replaced, and the lid (19) must by pressed down, the knob (28) can be pulled downwards by means of a spring, therefore pressing the lid holder (14) with the lid (19) onto the container (18) and closing the lid tight on the container. Once the hook (36) has been released, the lid holder is released. After the opening, a new lid (19) can be fitted. The lid holder (14) is compatible with the hook (36).

FIG. 3 shows a detail of a modification of FIG. 2. The lid holder (14) has a socket (26), in which latch (31) can be engaged with an adjustable device (32). When latch (31) is removed by means of the device (32), the assembly is released.

The container (18) is closed with the lid (19) by pulling and engaging the latch. The axial movement of the lid holder (14) is made possible by a corresponding movement in the articulation. The container is supported in at least three places of its bead edge (near 29).

It should be noted that the lid holder (14) can also be fitted with a pressing device (not shown) which presses the lid downwards, closing radially the axially-moving lid onto the container (18). The lid can be pressed uniformally on the container edge.

The opening angle of the lid holder must be calculated so that the contents can be thrown in without any problem. In general, articulation (12) is found behind the outer edge of the support (1).

To steer the different movements, foot switches or no-contact switches are preferred. They are not shown because they are generally known from the specialists.

What is claimed is:

1. Disposal equipment for infectious or otherwise contaminated waste, to be used for instance in hospitals, doctors' offices, laboratories and similar institutions; the waste is disposed of in a container (18) placed on a support (1), and when the container (18) is full it is closed tight by means of a lid (19) provided, with the specific feature that the lid (19) is held on the support (1) by means of a lid holder (14) which is actuated by a motorized drive (3) and which provides the opening and closing of the container (18), while the lid (19) is closed down loosely on the container (18) during a filling phase, and that another drive (4, 5; 27, 28) linked to the equipment (1) closes the lid holder (14), with the lid (19), down tight onto the container (18), and releases the lid (19) once the lid (19) has been connected to the container (18).

2. Equipment as per claim No. 1, in which the container to be closed has a beaded ridge (25), with the specific feature that the support (1) holds an open pick-up receptacle (7), the rim of which fits under the beaded ridge (25) of the container.

3. Equipment as per claim No. 2, with the specific feature that the pick-up receptacle (7) can be raised and lowered with the container (18).

4. Equipment as per claim No. 3, with the specific feature that the bottom (8) of the pick-up receptacle (7) rests on a plate (6) which can be raised and lowered by a drive (4).

5. Equipment as per claim No. 4, with the specific feature that the bottom (8) of the pick-up receptacle (7) fits tightly onto the plate (6).

6. Equipment as per claim No. 4, with the specific feature that the drive (3) for the rotation of the lid holder (14) and the drive (4) for raising and lowering the pick-up receptacle (7) are actuated by separate switches.

7. Equipment as per claim No. 1, with the specific feature that the lid holder (14) has spring clamps (17) for closing and releasing the lid (19).

8. Equipment as per claim No. 1, with the specific feature that the lid holder (14) can be tilted through a thrust gear (3, 9) which actuates a tilting articulation (12) by means of a motorized drive (3).

9. Equipment as per claim No. 1, with the specific feature that the support (1) is fitted with a moving, releasable clamping device (27) which fits into the compatible parts of the lid holder and which can be tightened together with the lid holder (14) against the support (1).

10. Equipment as per claim No. 1, with the specific feature that the lid holder (14) includes a pressing device which supports the lid (19) while it is being pressed on the container.

* * * * *